United States Patent
Bromer (10) Patent No.: US 9,132,015 B2
(45) Date of Patent: Sep. 15, 2015

(54) TUMID IMPLANT AND PUMP

(71) Applicant: EMPIRE TECHNOLOGY DEVELOPMENT LLC, Wilmington, DE (US)

(72) Inventor: Nicholas S. Bromer, Marietta, PA (US)

(73) Assignee: EMPIRE TECHNOLOGY DEVELOPMENT LLC, Wilmington (DE)

( * ) Notice: Subject to any disclaimer, the term of this patent is extended or adjusted under 35 U.S.C. 154(b) by 111 days.

(21) Appl. No.: 13/990,309

(22) PCT Filed: Nov. 5, 2012

(86) PCT No.: PCT/US2012/063499
§ 371 (c)(1),
(2) Date: May 29, 2013

(87) PCT Pub. No.: WO2014/070204
PCT Pub. Date: May 8, 2014

(65) Prior Publication Data
US 2014/0128974 A1    May 8, 2014

(51) Int. Cl.
*A61F 2/08*    (2006.01)
*A61F 2/38*    (2006.01)
(Continued)

(52) U.S. Cl.
CPC ............ *A61F 2/3872* (2013.01); *A61B 17/562* (2013.01); *A61F 2/30* (2013.01); *A61F 2/30756* (2013.01); *A61F 2/32* (2013.01);
(Continued)

(58) Field of Classification Search
CPC .............. A61F 2/3872; A61F 2002/30548; A61F 2002/30754; A61F 2/38; A61F 2002/30581; A61B 17/562

USPC ................................................. 623/14.12
See application file for complete search history.

(56) References Cited

U.S. PATENT DOCUMENTS 4,256,094 A    3/1981    Kapp et al.
5,269,811 A    12/1993    Hayes et al.
(Continued)

FOREIGN PATENT DOCUMENTS

WO    WO 2006097932    9/2006
WO    WO 2011005206 A1    1/2011
WO    PCT/US12/63499    11/2012

OTHER PUBLICATIONS

International Searching Authority, International Search Report and Written Opinion for PCT/US12/63499, Apr. 19, 2013, 22 pages.

*Primary Examiner* — Bruce E Snow
*Assistant Examiner* — Brian Dukert
(74) *Attorney, Agent, or Firm* — Jensen & Puntigam, PS (57) ABSTRACT

Technologies related to tumid implants and pumps are generally described. In some examples, a tumid implant device may comprise an enclosed sack membrane adapted to fit between bones in a joint. Articulation of the joint may cause a first layer of the membrane to move through a first boundary section into a second layer of the membrane, while the second layer moves through a second boundary section into the first layer. A working fluid may be disposed inside the sack membrane, and a reservoir may optionally be coupled to the membrane via a gate. The working fluid may be expelled from the sack membrane into the reservoir, and may re-enter the sack membrane from the reservoir in response to changes in pressure in the joint. The working fluid may be conducted into the reservoir or sack membrane by a pump, and several artery pump designs are disclosed.

19 Claims, 5 Drawing Sheets

(51) Int. Cl.
*A61F 2/30* (2006.01)
*A61B 17/56* (2006.01)
*A61F 2/32* (2006.01)
*A61F 2/48* (2006.01)

(52) U.S. Cl.
CPC ........ *A61F 2/38* (2013.01); *A61F 2002/30548* (2013.01); *A61F 2002/30581* (2013.01); *A61F 2002/30754* (2013.01); *A61F 2002/485* (2013.01)

(56) References Cited

U.S. PATENT DOCUMENTS

| | | | |
|---|---|---|---|
| 5,676,162 | A | 10/1997 | Larson, Jr. et al. |
| 2004/0093087 | A1 | 5/2004 | Ferree et al. |
| 2008/0097606 | A1 | 4/2008 | Cragg et al. |
| 2009/0312807 | A1 | 12/2009 | Boudreault et al. |
| 2010/0010531 | A1 | 1/2010 | Shalon et al. |
| 2011/0288642 | A1* | 11/2011 | Forsell ............ 623/14.12 |

* cited by examiner

TUMID IMPLANT AND PUMP

CROSS-REFERENCE TO RELATED APPLICATION

The present application is a U.S. National stage filing under 35 U.S.C. §371 of International Application PCT/US 12/63499, entitled "TUMID IMPLANT AND PUMP", filed on Nov. 5, 2012, the entire contents of which are incorporated herein by reference.

BACKGROUND

Unless otherwise indicated herein, the materials described in this section are not prior art to the claims in this application and are not admitted to be prior art by inclusion in this section.

Joint implants may be adapted for a variety of joint types found in humans as well as other animals. For example, implants have been made and are now in use for human knee and hip joints. Current implant types include complete joint replacement implants, which are inserted into organisms to replace the surfaces of a joint, as well as partial joint replacement implants designed to replace diseased or damaged joint surfaces with metal and plastic components shaped to allow continued motion of the joint.

Joint implants are generally inserted to relieve the pain and disability of osteoarthritis. Joint implants may also be inserted for other joint conditions, such as rheumatoid arthritis, psoriatic arthritis, or to address injuries such as sports, work, car or other accident related injuries. Other major causes of debilitating pain which may warrant joint implants include meniscus tears, cartilage defects, and ligament tears.

Complete and partial joint replacement implants may not provide the same even pressure and smooth bearing that a patient's original joint does. In particular, tears and breaks in the cartilage or the meniscus are difficult to make smooth enough to obviate pain and further damage in a joint that is fitted with an implant. Surgical attempts to create a new bearing surface as good as the original often do not succeed. As a result, in addition to the often substantial postoperative pain and long recovery periods associated with joint implant operations, patients may experience ongoing joint pain and may never experience a return to full mobility. There is a need to develop improved joint implants to provide meaningful health and quality of life benefits to at least some patients.

SUMMARY

The present disclosure generally describes technologies including devices and methods relating to a tumid implant and pump. Some example tumid implant devices may comprise an enclosed sack membrane adapted to fit between bones in a joint. The enclosed sack membrane may comprise a first concave layer adapted to fit adjacent a first bone in the joint, and a second concave layer adapted to fit adjacent a second bone in the joint. For example, when the joint is a human knee joint, the first bone may be a femur, the second bone may be a tibia, and the first concave layer may be adapted to fit adjacent an epiphysis section of the femur while the second concave layer may be adapted to fit adjacent a meniscus and tibia in the knee. The first and second concave layers may be oriented with concavity facing a same direction.

The first and second concave layers may have a separation distance from one another and may thereby apply a separation between the first and second bones in the joint. The first and second concave layers may have substantially elliptical boundaries, and a curved boundary section may adjoin the first and second concave layers around the elliptical boundaries thereof. The curved boundary section may comprise a curved section of the enclosed sack membrane between the first and second concave layers such that articulation of the joint causes the first concave layer to move through a first portion of the curved boundary section into the second concave layer, and articulation of the joint causes the second concave layer to move through a second portion of the curved boundary section into the first concave layer. A working fluid may be disposed within the enclosed sack membrane.

The enclosed sack membrane may be adapted to respond to changes in pressure applied between the bones in the joint. For example, in some embodiments, the enclosed sack membrane may comprise an elastic material adapted to stretch in response to an increase in pressure applied between the bones in the joint, and adapted to contract in response to a release in pressure applied between the bones in the joint. In some embodiments, a gate in the enclosed sack membrane may be adapted to allow the working fluid to escape from the enclosed sack membrane in response to an increase in pressure applied between the bones in the joint. A reservoir filled with the working fluid may be coupled with the gate. The reservoir may be adapted to apply a backpressure at the gate, so that the working fluid in the enclosed sack membrane escapes through the gate and into the reservoir in response to an increase in pressure applied between the bones in the joint, and the working fluid in the reservoir flows back through the gate and into the enclosed sack membrane under the backpressure in response to a release in pressure applied between the bones in the joint. In some embodiments, a pressure capillary may be adapted to conduct the working fluid from a pump into the reservoir.

Some example pump devices may be configured as artery pump implant devices. A first example artery pump implant device may comprise an inextensible cylindrical cuff adapted to substantially surround an artery segment, and a flexible cylindrical bladder adapted between the inextensible cylindrical cuff and the artery segment and having a bladder volume adapted to expand and contract inversely with expansion and contraction of the artery segment. The artery segment may comprise, for example, a segment of the popliteal artery near the human knee joint. A first valve may be adapted to allow flow of a working fluid out of the flexible cylindrical bladder and to inhibit flow of the working fluid into the flexible cylindrical bladder, and a second valve may be adapted to allow flow of a working fluid into the flexible cylindrical bladder and to inhibit flow of the working fluid out of the bladder.

As the bladder volume expands, the working fluid may be drawn into the bladder through the second valve. As the bladder volume contracts, the working fluid may be expelled from the bladder through the first valve. An intake capillary coupled with the second valve may be adapted to conduct the working fluid into the flexible cylindrical bladder. A pressure capillary coupled with the first valve may be adapted to conduct the working fluid into the tumid implant device—such as into the enclosed sack membrane or reservoir.

A second example artery pump implant device may comprise a flexible cylindrical collar adapted to substantially surround an artery segment. The flexible cylindrical collar may comprise a variable gap oriented substantially parallel to a direction of blood flow through the artery. The flexible cylindrical collar may be adapted to flex in unison with expansion and contraction of the artery, thereby expanding and contracting a width of the variable gap.

A piston pump may be affixed on an outer surface of the flexible cylindrical collar. The piston pump may extend across the variable gap and may be oriented substantially perpendicular to the variable gap. The piston pump may comprise, inter alia, a piston pump housing affixed to the flexible cylindrical collar on a first side of the variable gap, and a piston affixed to a piston rod, wherein the piston rod may be affixed to the flexible cylindrical collar on a second side of the variable gap, and the piston rod may extend into the piston pump housing, so that the piston rod is affixed to the piston within the piston pump housing.

The piston may be adapted to slide back and forth within the piston pump housing in a direction substantially perpendicular to a flow of blood through the artery as the width of the variable gap expands and contracts. A first valve may be adapted to allow flow of a working fluid out of the piston pump housing and to inhibit flow of the working fluid into the piston pump housing, and a second valve may be adapted to allow flow of the working fluid into the piston pump housing and to inhibit flow of the working fluid out of the piston pump housing.

As the artery contracts, the working fluid may be drawn into the piston pump housing through the second valve, without also drawing the working fluid through the first valve, because the flexible cylindrical collar may return to its original shape, e.g. an original cylindrical shape having a diameter matching that of the fully contracted artery, due to elasticity of the flexible cylindrical collar, pressure of surrounding tissues, or other factors. As the artery expands, the working fluid may be expelled under pressure from the piston pump housing through the first valve, without also expelling the working fluid through the second valve. As with the bladder pump design, an intake capillary coupled with the second valve may be adapted to conduct the working fluid into the piston pump housing. A pressure capillary coupled with the first valve may be adapted to conduct the working fluid into the tumid implant device—such as into the enclosed sack membrane or reservoir.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and made part of this disclosure.

The present disclosure is generally drawn, inter alia, to technologies including methods, devices, and/or systems relating to tumid implants and pumps. In some examples, a tumid implant device may comprise an enclosed sack membrane adapted to fit between bones in a joint. Articulation of the joint may cause a first layer of the membrane to move through a first boundary section into a second layer of the sack membrane, while the second layer moves through a second boundary section into the first layer. A working fluid may be disposed inside the sack membrane, and a reservoir may optionally be coupled to the sack membrane via a gate. The working fluid may be expelled from the sack membrane into the reservoir, and may re-enter the sack membrane from the reservoir in response to changes in pressure in the joint. The working fluid may be conducted into the reservoir or sack membrane by a pump, and several artery pump designs are disclosed.

Figure 1:
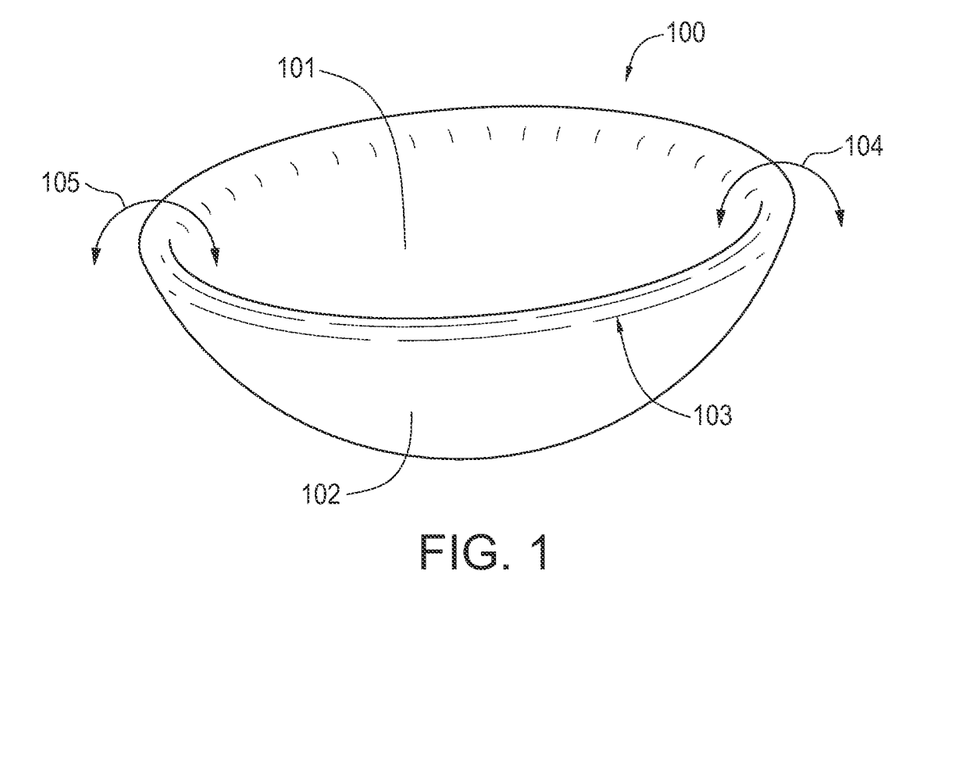
FIG. 1 is a diagram illustrating an example tumid implant device comprising an enclosed sack membrane.

FIG. 1 is a diagram illustrating an example tumid implant device comprising an enclosed sack membrane, arranged in accordance with at least some embodiments of the present disclosure. A tumid implant may include an enclosed sack membrane 100 which comprises a first concave layer 101, a second concave layer 102, and a curved boundary section 103 adjoining first and second concave layers 101 and 102. Arrows 104 and 105 indicate motion of the first and second concave layers 101 and 102 as described further below.

The enclosed sack membrane may resemble a deflated ball (such as a football, soccer ball, etc.) where one half of the ball is depressed into the other half of the ball. Arrows 104 and 105 arching over two sides of curved boundary section 103 in FIG. 1 indicate that when appropriate forces are applied to the surfaces of tumid implant 100, first concave layer 101 may move through curved boundary section 103 into second concave layer 102. For example, first concave layer 101 may "slide" to the left (relative to second concave layer 102) in FIG. 1, and first concave layer 101 may "roll" up and over the left-side portion of curved boundary section 103 into second concave layer 102. Similarly, second concave layer 102 may simultaneously "slide" to the right (relative to first concave layer 101) in FIG. 1, and second concave layer 102 may "roll" up and over the right-side portion of curved boundary section 103 into first concave layer 101. Thus when tumid implant 100 is disposed between the bones of a joint, and the joint articulates, first and second concave layers 101 and 102 may accommodate the articulation substantially without the surfaces of the tumid implant 100 sliding across the bone, cartilage, or other surfaces in the joint, while separation between first and second concave layers 101 and 102 also prevents friction between bones as the joint articulates.

Figure 2:
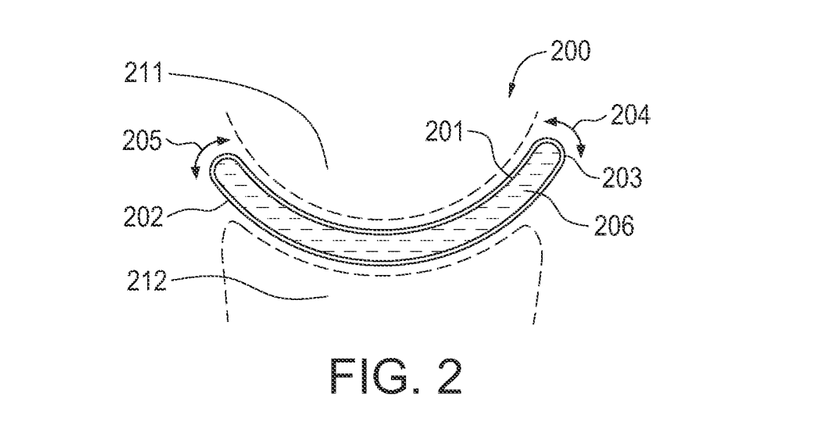
FIG. 2 is a diagram illustrating a cross sectional view of the example tumid implant device disposed between bones in a joint.

FIG. 2 is a diagram illustrating a cross sectional view of an example tumid implant device disposed between bones in a joint, arranged in accordance with at least some embodiments of the present disclosure. A sack membrane 200 may be disposed between a first bone 211 and a second bone 212. The cross-sectional view provided by FIG. 2 shows enclosed sack membrane 200 comprising a first concave layer 201 as the top layer of sack membrane 200, and a second concave layer 202, e.g., as the bottom layer of sack membrane 200. A curved boundary section 203 adjoins first and second concave layers 201 and 202.

A fluid 206 may be disposed inside sack membrane 200. Fluid 206 may be referred to herein as a working fluid. Fluid 206 may comprise, for example, any non-toxic liquid which would not harm the host organism in the event of escape from sack membrane 200. Water, salt water, and/or lymph drawn from tissue around the tumid implant device 100 may be used as fluid 206 in some embodiments. Curved arrows 204 and 205 indicate motion of first and second concave layers 201 and 202 as bones 211, 212 articulate.

Figure 3:
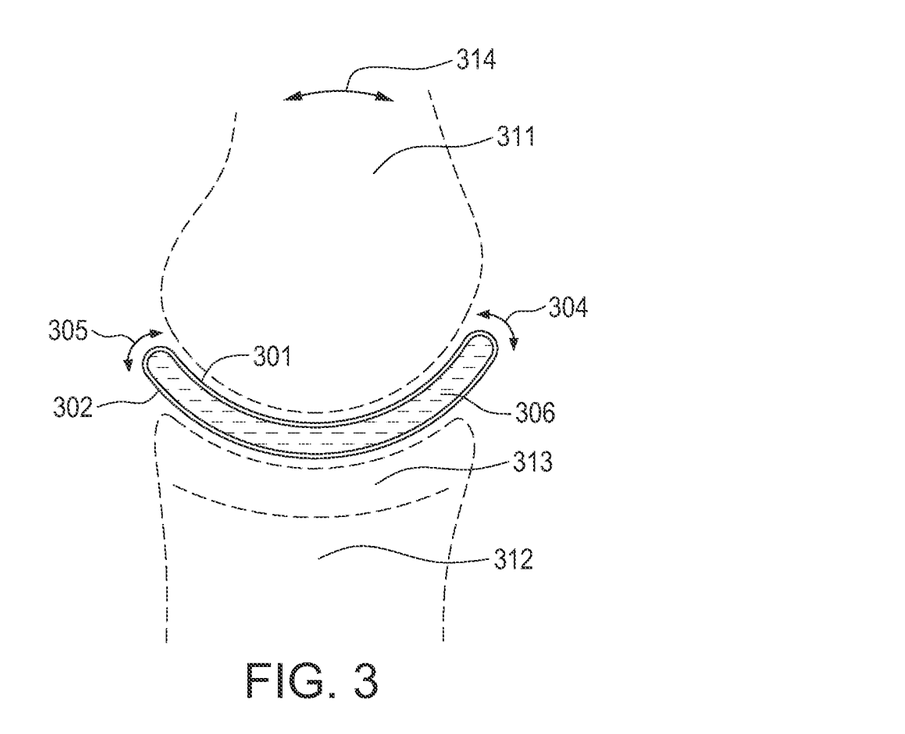
FIG. 3 is a diagram illustrating a cross sectional view of the example tumid implant device disposed between bones in a human knee joint.

FIG. 3 is a diagram illustrating a cross sectional view of example tumid implant device disposed between bones in a human knee joint, arranged in accordance with at least some embodiments of the present disclosure. The bones in the knee joint include a femur 311 and a tibia 312. A meniscus 313 is also illustrated in the joint, in the top section of tibia 312. A sack membrane may be positioned between femur 311 and tibia 312. For example, a first concave layer 301 of the sack membrane may be positioned substantially adjacent femur 311, and a second concave layer 302 may be positioned substantially adjacent tibia 312. A fluid 306 may be disposed inside the sack membrane. Curved arrows 304 and 305 indicate motion of first and second concave layers 301 and 302 as femur 311 and tibia 312 articulate, as indicated by curved arrow 314.

The human knee joint is illustrated in FIG. 3 and may be used in various examples herein, however it is to be understood that this disclosure is not limited human knee implants, and embodiments of this disclosure may provide implants for other human joints, as well as joints in other animals. In the human knee joint, meniscus 313 may separate some or all of second concave layer 302 from tibia 312, however, as the terms "adjacent" and "substantially adjacent" are used herein, second concave layer 302 may be considered to be adjacent tibia 312, regardless of the presence of meniscus 313 between second concave layer 302 and tibia 312. The same idea applies to cartilage and other non-bony tissues on femur 311 and tibia 312, which might contact the sack membrane.

In a human knee joint, first concave layer 301 may be adapted to fit adjacent an epiphysis section of femur 311, and second concave layer 302 may be adapted to fit adjacent meniscus 313 and tibia 312 in the knee. For example, first and second concave layers 301, 302 may be oriented with concavity facing a same direction, as illustrated in FIG. 3. First and second concave layers 301, 302 may also have diameter of an appropriate dimension for the human knee, e.g. a diameter in the range of about 2 to about 6 inches, depending on the size of the particular joint and the extent of bone surfaces in contact with first and second concave layers 301, 302. Smaller sizes may be appropriate for other joints, e.g., the elbow. The separation distance between first and second concave layers 301, 302 may be on a scale appropriate for the human knee, e.g., a separation distance in the range of about $\frac{1}{16}^{th}$ to $\frac{1}{4}^{th}$ inch, depending on the size of the joint. However, it should be emphasized that embodiments of this disclosure designed for other joints may be adapted differently, and may for example provide different diameters, different separation distances, and different concavity orientations from those that may be applicable for human knee joints. The ideal separation distance for some joints may be that which maintains a continuous layer of fluid between first and second concave layers 301, 302 without distending the joint more than necessary. The separation distance might vary between individuals, between different joint types, and between different types of joint damage.

With reference to FIG. 1-FIG. 3, in some embodiments, tumid implant devices may comprise sack membranes without a gate, a reservoir, a pump, and/or other structures described in connection with FIG. 4-FIG. 7. The term "sealed sack membrane" may be used herein to refer to sack membranes that do not have any openings allowing entry or exit of fluid such as 206 or 306. Other embodiments may include a sack membrane as well as a gate, a reservoir, a pump, and/or other structures as described in connection with FIG. 4-FIG. 7. The terms "sack membrane" and "enclosed sack membrane" as used herein include both sealed sack membranes as well as sack membranes that are fitted with openings, such as a gate, allowing entry and exit of fluid.

As illustrated in FIG. 1-FIG. 3, enclosed sack membranes may be adapted to fit between bones in a joint. First and second concave layers may have a separation distance from one another and may thereby apply a separation between the first and second bones in the joint. The separation distance can be seen for example in FIG. 2 and FIG. 3, wherein the separation distance may comprise the distance between the top and bottom layers of the illustrated sack membranes. In real-world applications, the separation distance between first and second concave layers may be non-uniform.

First and second concave layers may have substantially elliptical boundaries. For example, as shown in FIG. 1, the boundaries of first and second concave layers 101 and 102 may be defined by curved boundary section 103. Curved boundary section 103 may form a complete circle, or other elliptical shape such as an ellipse or a football shape, as curved boundary section 103 adjoins the first and second concave layers 101 and 102 around the elliptical boundaries thereof. The term "elliptical" as used herein includes any conic-section shapes including circles, ellipses, generally oval or ovoid shapes, and non-smooth ovals such as for example that of an American football.

Curved boundary section 103 comprises a curved section of enclosed sack membrane 100 between first and second concave layers 101 and 102 such that articulation of the joint causes first concave layer 101 to move through a first portion of curved boundary section 103 into second concave layer 102, and articulation of the joint causes second concave layer 102 to move through a second portion of curved boundary section 103 into first concave layer 101. For example, with reference to FIG. 2, on a first side of FIG. 2, e.g., on the right, the bottom layer 202 of enclosed sack membrane 200 may translate with an action similar to a conveyor belt, through the curved boundary section 203 to thereby become part of the top layer 201 of the enclosed sack membrane 200. Meanwhile, on the opposite side of enclosed sack membrane 200, e.g., on the left, the top layer 201 of enclosed sack membrane 200 may translate through the curved boundary section 203 to thereby become part of the bottom layer 202.

In some embodiments, enclosed sack membrane 200 may be adapted to respond to changes in pressure applied between bones 211 and 212 in the joint. For example, in some embodiments, enclosed sack membrane 200 may comprise an elastic material adapted to stretch in response to an increase in pressure applied between bones 211 and 212 in the joint. For example, when sack membrane 200 is in a knee or hip joint, and the patient steps down off a curb, there is an increase in pressure applied between bones 211 and 212. The elastic material of enclosed sack membrane 200 may be adapted to contract in response to a release in pressure applied between bones 211 and 212 in the joint. For example, when the patient subsequently transfers weight to their other leg, there is a release in pressure applied between bones 211 and 212. The use of elastic materials adapted to stretch and contract is considered particularly applicable in the case of sealed sack membrane embodiments, because sealed sack membranes, by definition, cannot release fluid 206 in response to changes in pressure. However, elastic materials may also be useful in the context of any of the enclosed sack membrane embodiments described herein.

Any of a wide variety of materials now known, or as may be developed in the future, may be incorporated into enclosed sack membranes. In some embodiments, nylon and/or Kevlar fabrics may be used to provide a strong and flexible material for enclosed sack membranes. Such fabrics may be combined with flexible plastic coatings. Strong, flexible, highly durable materials, which may also provide smooth surfaces inside and/or outside of enclosed sack membranes, may be preferred for some embodiments. In some embodiments, curved boundary section 203 may be reinforced and/or made from different materials to provide increased durability and/or flexibility to withstand repeated bending and unbending of enclosed sack membrane 200 at curved boundary section 203. Other materials appropriate for use in enclosed sack membrane 200 may include, but are not limited to, materials that are generally strong in tension, flexible, and also leak proof Materials may comprise woven fabrics coated with one or more liquid-impervious layers on the inside. Fabrics comprising many fine threads can generally achieve sufficient flexibility. Fabrics may be woven from high-tensile-strength fibers such as nylon, polyester, tetrafluoroethylene, polyacetal, stainless steel, or other fibers that can be obtained as sterile fabrics and which are bio-compatible, or mixtures of such fibers. Fabrics may be coated with an elastomer such as silicone or polyurethane layered on the inside to reduce leakage. The enclosed sack membrane 200 may also be coated on the outside to prevent chafing or to increase friction as needed with various materials such as the bones or cartilage in the joint.

In some embodiments, to prevent migration of enclosed sack membrane 200 within a joint, enclosed sack membrane 200 may be anchored to adjacent bones. Anchor points may be selected as points on first and second concave layers 201 and 202 that do not move through curved boundary section 203 during normal articulation of the joint, e.g., the central portions of the upper and lower joint bearing surfaces of the femur 311 and tibia 312, or points near or along the curved boundary section 203 that do not translate because they lie at or near to the border between the opposing "rolls" indicated by curved arrows in the figures, where there may be no rolling of curved boundary section 203. Fixture portions of sack membrane 200, fasteners, or other attaching/anchoring means (not illustrated) may be located at such "non-rolling" points to act as anchors. Anchor points on first and second concave layers 201 and 202 may be glued or otherwise fastened to first and second bones 211 and 212, respectively.

Materials appropriate for use in anchoring enclosed sack membrane 200 to adjacent bones may include, but are not limited to, medical versions of adhesives such as cyanoacrylate and/or UV-curing adhesives that are bio-compatible. Silicones are widely used in medical applications due to their biocompatibility and can be used as adhesives. Mechanical devices such as stainless steel or titanium bone screws can be used at the non-rolling edges of sack membrane 200, and thickened flaps with pre-existing holes can be provided on the sack membrane 200 for attaching with screws or other fasteners (not illustrated).

Figure 4:
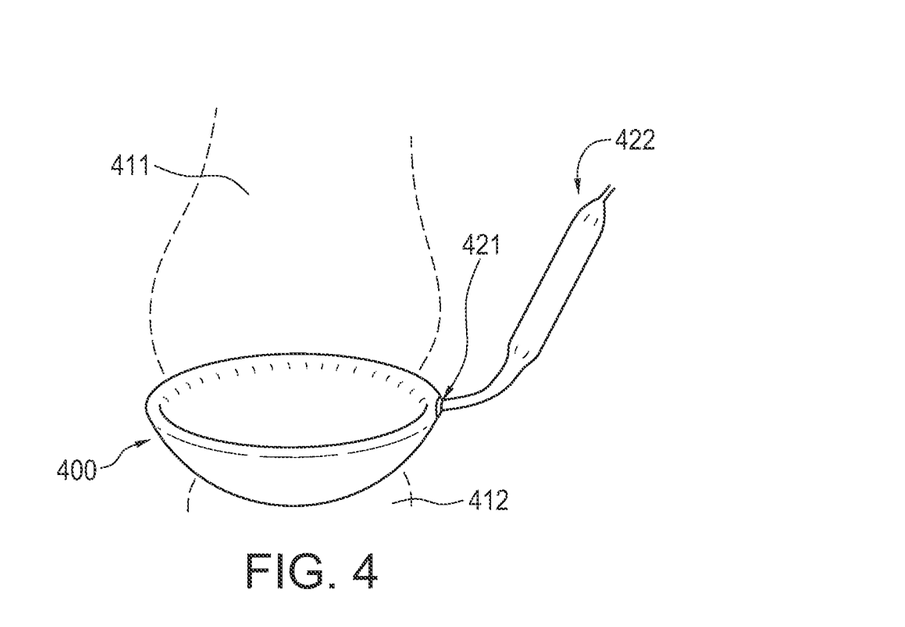
FIG. 4 is a diagram illustrating an example tumid implant device comprising an enclosed sack membrane coupled with a reservoir.

FIG. 4 is a diagram illustrating an example tumid implant device comprising an enclosed sack membrane coupled with a reservoir, arranged in accordance with at least some embodiments of the present disclosure. A gate 421 in enclosed sack membrane 400 may be adapted to allow working fluid to escape from enclosed sack membrane 400 in response to an increase in pressure applied between bones 411 and 412 in the joint. Gate 421 may be adapted to not allow working fluid to escape from enclosed sack membrane 400 under normal pressure conditions in the joint, but to release fluid at or above a gate threshold pressure. The gate 421 may be sized to control a flow rate at which working fluid escapes from and re-enters enclosed sack membrane 400. Gate 421 may include one-way valves, pressure-actuated "safety" valves, and/or other hydraulic components selected to optimize its function. A reservoir 422 filled with working fluid may be coupled with gate 421. Reservoir 422 may be adapted to apply a backpressure at gate 421, so that working fluid in enclosed sack membrane 400 escapes through gate 421 and into reservoir 422 in response to an increase in pressure applied between the bones 411 and 412 in the joint, and working fluid in reservoir 422 flows through gate 421 and into enclosed sack membrane 400 under the backpressure applied by reservoir 422 in response to a release in pressure applied between the bones 411 and 412 in the joint. Reservoir 422 may absorb impact energy by taking in pressurized working fluid (thereby removing energy from the sack membrane 400) and reservoir 422 may also protect the sack membrane 400 from pressure spikes.

In some embodiments, tumid implant devices may comprise sack membrane 400, gate 421, and reservoir 422, without a pump and/or other structures described in connection with FIG. 5-FIG. 7. In embodiments without a pump, sack membrane 400, gate 421, and reservoir 422 may be configured as a sealed system from which fluid may not escape. In embodiments comprising a pump, sealed embodiments that are configured to circulate fluid within tumid implant devices, as well as unsealed embodiments that circulate fluid between the host organism and tumid implant devices are described herein.

The backpressure applied by reservoir 422 at gate 421 may be variable. For example, in some embodiments, a "neutral" state of a tumid implant device may be defined by little or no backpressure—e.g., a same or similar pressure in reservoir 422 and sack membrane 400. The neutral state may be normally achieved when there is baseline pressure in the joint, e.g., when the host organism is sitting or lying down and so there is little or no load on the joint.

A "forward pressure" state of a tumid implant device may be defined by a higher pressure in sack membrane 400 than in reservoir 422. The forward pressure state may be entered as a result of increased pressure in the sack membrane 400, e.g., when the host organism steps off a curb or otherwise loads the joint with weight. The forward pressure state may force fluid out of sack membrane 400 through gate 421 and into reservoir 422.

A "backpressure" state of a tumid implant device may be defined by a higher pressure in reservoir 422 than in sack membrane 400. The backpressure state may be entered as a result of decreased pressure in the sack membrane 400 following a forward pressure state, e.g., when the host organism transfers weight off of the joint (e.g., to another leg) or otherwise reduces the load on the joint. The backpressure state may also result from increased pressure in reservoir 422 due to elastic stretching of reservoir 422 during escape of fluid into reservoir 422 in the forward pressure state. The backpressure state may cause fluid to escape reservoir 422 through gate 421 and into sack membrane 400. In some embodiments, reservoir 422 may be adapted to apply a backpressure at gate 421 for example by incorporating elastic materials that stretch in response to increased working fluid volume in reservoir 422, such as when working fluid enters reservoir 422 from sack membrane 400. Reservoir 422 may expand in volume similar to inflation of a balloon, and reservoir 422 may then apply a backpressure at gate 421 sufficient to force working fluid back through gate 421 and into enclosed sack membrane 400. In some embodiments, reservoir 422 may be made from an elastic material such as surgical tubing with a diameter, volume, and sidewall thickness selected for desired volume and elasticity of reservoir 422. Materials appropriate for use in reservoir 422 may include, but are not limited to, materials with lower tensile strength to allow stretching and corresponding increase in the volume of reservoir 422 under pressure. Suitable materials may comprise elastomers such as silicone, for example.

It will be appreciated that gate 421 may comprise a two-way gate adapted to allow working fluid to escape and enter sack membrane 400. In some embodiments, two or more one-way gates, e.g., each allowing flow of fluid in opposite directions, may be employed in place of a two-way gate. Gate 421 may be arranged as appropriate for particular embodiments. For example, flow rates allowable by gate 421 in forward and backward flow directions (out of and into sack membrane 400, respectively), and pressure differences to which gate 421 responds in forward and backward directions, may be adapted to suit particular embodiments. Also, any gate structures now known or as may be developed in the future may be incorporated into gate 421. Furthermore, in some embodiments, gate 421 may comprise an open orifice into sack membrane 400, without any more complex flow control structures. The size of the gate orifice may effectively control flow forward and backward fluid flow rates. It will also be appreciated that in some embodiments, tumid implant devices may comprise a single sack membrane 400 fitted with multiple gates 421 and reservoirs 422.

Figure 5:
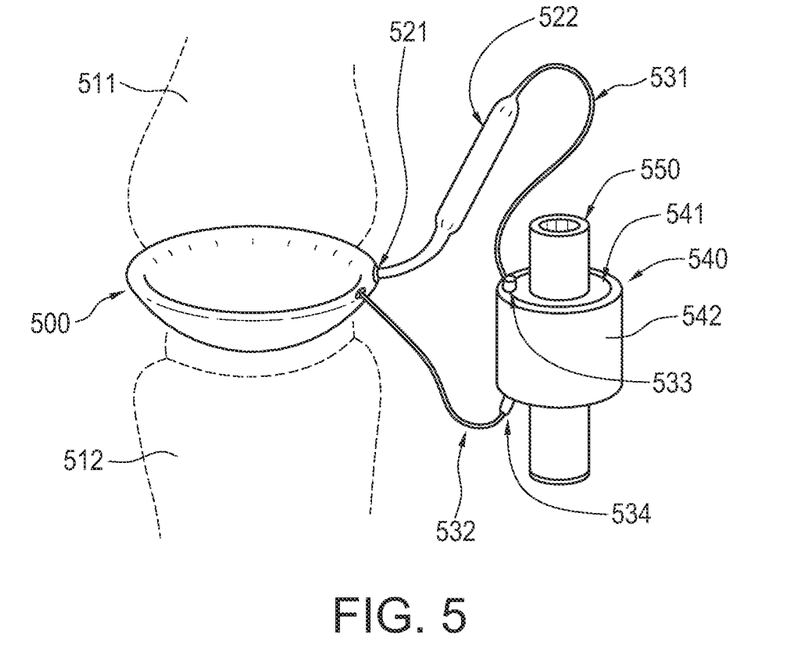
FIG. 5 is a diagram illustrating an example tumid implant device coupled with a pump.

FIG. 5 is a diagram illustrating an example tumid implant device coupled with a pump, arranged in accordance with at least some embodiments of the present disclosure. FIG. 5 includes a sack membrane 500, a gate 521, and a reservoir 522. Sack membrane 500 is fitted between bones 511 and 512. A pressure capillary 531 is coupled between reservoir 522 and a first valve 533 on a pump 540. An intake capillary 532 is coupled between sack membrane 500 and a second valve 534 on pump 540. Pump 540 comprises a bladder-type artery pump including a flexible cylindrical bladder 541 surrounding an artery 550 and an inextensible cylindrical cuff 542 surrounding flexible cylindrical bladder 541.

In general, with reference to FIG. 5, working fluid may be exchanged between sack membrane 500 and reservoir 522 in response to changes in pressure in the joint, as described above in connection with FIG. 4. In addition, embodiments according to FIG. 5 may be configured to circulate fluid within the tumid implant device, e.g., by drawing fluid out of sack membrane 500, through intake capillary 532, and into pump 540, and supplying fluid through pressure capillary 531 into reservoir 522. Embodiments according to FIG. 5 may also be configured to adjust fill and/or pressure within sack membrane 500 and reservoir 522 to maintain desired optimal fill and/or pressure properties in the tumid implant device.

Pump 540 may use expansion and contraction of artery 550 to pump working fluid. In embodiments applied to the human knee joint, pump 540 may be adapted to fit the popliteal artery of the human knee. In other embodiments, pump 540 may be adapted to fit other arteries. Bladder-type artery pumps may be similar in some respects to a blood-pressure cuff, with an inextensible belt cylindrical cuff 542 wrapped around artery 550 and, inside inextensible cylindrical cuff 542, a flexible cylindrical bladder 541 that expands and contracts with the movement of the outside of artery 550 as artery 550 pulses. In other words, the bladder volume may be adapted to expand and contract inversely with expansion and contraction of the artery segment.

When artery 550 expands, inextensible cylindrical cuff 542 may be adapted to substantially surround an artery segment and inextensible cylindrical cuff 502 may remain of substantially fixed diameter or circumferential length, thereby effectively reducing available volume for flexible cylindrical bladder 541 between artery 550 and inextensible cylindrical cuff 542. As a result, the volume of flexible cylindrical bladder 541 adapted between inextensible cylindrical cuff 542 and the artery segment may contract as artery 550 expands. Materials appropriate for use in inextensible cylindrical cuff 542 may include, but are not limited to, materials with generally high tensile strength in the circumferential direction, to resist expansion. Materials may also be flexible, e.g., many fabrics may have desirable material properties. In FIG. 5 the cuff 542 is shown as a piece separate from the bladder 541, e.g., as rigid resin tube that can be assembled around the artery 550. While such embodiments are possible, other embodiments may incorporate cuff 542 and bladder 541 into a single piece, as described below.

Flexible cylindrical bladder 541 may be made from compressible and/or elastic material that returns to its original shape when compressive forces are relaxed, to support expansion of bladder 541 to maintain contact with both inextensible cylindrical cuff 542 and artery 550 as artery 550 contracts. Materials appropriate for use in bladder 541 may include, but are not limited to, silicone or other elastomers. Because the cuff 542 can be flexible, in some embodiments cuff 542 may be combined with the bladder 541 in one piece that can be wrapped around artery 550 and end-fastened, much like a blood-pressure cuff. Suitable materials for such embodiments may comprise silicone or other elastomers in bladder 541, which may be reinforced on the outside with inelastic tensile fibers of a fabric material such as a polyester fabric to impart resistance to stretching by cuff 542. Silicone or other elastomers may also be used for pressure and intake capillaries 531 and 532. In some embodiments, bladder 541, enclosed sack membrane 500, pressure and intake capillaries 531 and 532, and/or reservoir 522 may be made form a same material formed as a one-piece, leak-resistant structure.

Bladder 541 may be coupled with first valve 533 allowing fluid to flow out of bladder 541, and second valve 534 allowing fluid to flow into bladder 541, so that pump 540 is effective to pump fluid, albeit in small quantities, as the volume of bladder 541 expands and contracts. First and second valves 533 and 534 may comprise, for example, one-way or check valves. The systolic pressure of blood is generally about two (2) pounds per square inch (psi), and so pressures produced by bladder-type artery pump 540 may generally be in the range of around 2 psi, although variations may potentially be configured to produce different pressures.

First valve 533 may be adapted to allow flow of working fluid out of bladder 541 and into pressure capillary 531 and reservoir 522, and first valve 533 may be adapted to inhibit flow of working fluid in the opposite direction, i.e., from reservoir 522 into bladder 541. Meanwhile, second valve 534 may be adapted to allow flow of working fluid from sack membrane 500 and intake capillary 532 into bladder 541, and second valve 534 may be adapted to inhibit flow of working fluid in the opposite direction, i.e., out of bladder 541 and into intake capillary 532. As a result, the expansion and contraction of bladder 541 may be effective to draw fluid from intake capillary 532 and expel fluid into pressure capillary 531.

In some embodiments, intake capillary 532 and pressure capillary 531 may be made from a strong, flexible material which may also have some elasticity, such as surgical tubing with a diameter and sidewall thickness selected for desired elasticity of intake capillary 532 or pressure capillary 531. Materials appropriate for use in intake capillary 532 and pressure capillary 531 may include, but are not limited to, silicone or other elastomers as noted above. In this disclosure the term "capillary" does not imply any limitation of inside diameter or of flow rate.

In some embodiments, second valve 534 may be adapted to inhibit flow of working fluid out of bladder 541 and into intake capillary 532 up to a design pressure. Above the desired design pressure, second valve 534 may be adapted to allow backflow of working fluid out of bladder 541 and into intake capillary 532. As a result, overpressure within pressure capillary 531 and reservoir 522 can be avoided, without also restricting flow of blood through artery 550. When pressure in bladder 541 meets or exceeds the design pressure, fluid may be drawn into pump 540 from intake capillary 532, and may be expelled out of pump 540 into intake capillary 532 as bladder 541 expands and contracts. Alternatively, bladder 541, intake capillary 532, pressure capillary 531, reservoir 522 and/or sack membrane 500 may be fitted with an overpressure safety valve configured to release fluid into the host organism in response to overpressure that exceeds design specifications for the tumid implant device and/or any particular component thereof.

In some embodiments, pump 540 may be adapted to pressurize reservoir 522. For example, pump 540 may be adapted to apply a minimal baseline pressure within reservoir 522 so that reservoir 522 remains full without significantly stretching the material of reservoir 522. As a result, any flow of fluid into reservoir 522 from sack membrane 500 may be effective to stretch reservoir 522 and generate backpressure which eventually results in return of fluid from reservoir 522 into sack membrane 500. A minimal baseline pressure applied by pump 540 may be adapted to suit particular embodiments. Volume and pressure outputs of bladder-type artery pump 540 may generally be adapted through selection of a length of bladder 541 and cuff 542. For example, a pump 540 that is $\frac{1}{4}^{th}$ inch in length will generally have different properties than a pump 540 that is $\frac{1}{2}$ inch in length. For example, longer pump configurations may be effective to produce larger fluid flow rates than shorter pump configurations. Also, thinner bladder 541 configurations wherein the inner diameter of cuff 542 is closer to the outer diameter of artery 550 may be effective to increase efficiency or output pressure of pump 540.

In some embodiments, any of the components illustrated in FIG. 5 may be fitted with a fluid release valve. For example, sack membrane 500 may be fitted with a fluid release valve that releases fluid from the tumid implant device and into the host organism under a selected release pressure. The selected release pressure may or may not include pressures normally experienced due to "normal" increases in pressure such as from stepping off a curb, walking down stairs, or otherwise loading the joint. When fitted with a fluid release valve, the tumid implant device may or may not also include reservoir 522, as operation of pump 540 may be effective to apply sufficient backpressure at gate 521 to refill sack membrane 500 after fluid release. Furthermore, pump 540 may be adapted to draw fluid from sources other than sack membrane 500, such as lymph fluid drawn from the host organism, to replace fluid expelled from the tumid implant device from the fluid release valve. In some embodiments, intake capillary 532 may be fitted with a lymph filter as described in connection with FIG. 7, and pump 540 may be thereby adapted to draw lymph into the pump 540 from a body in which the pump 540 is implanted, through the lymph filter, intake capillary 532, and second valve 534. In some embodiments, intake capillary 532 may be coupled with reservoir 522 instead of, or in addition to, being coupled with sack membrane 500.

In some embodiments, intake capillary 532 may be fitted with a gate and reservoir, configured to serve similar functions as gate 521 and reservoir 522, described herein. Also, in some embodiments, sack membrane 500 may be adapted to intentionally "leak" fluid, e.g., to provide circulation of fluid out of the tumid implant device. In such embodiments, pump 540 may be adapted to draw fluid from sources other than sack membrane 500, such as through a lymph filter as noted above.

This disclosure appreciates that artery pump designs disclosed herein, such as the bladder-type and piston-type artery pumps and variants thereof, such as any pump adapted to translate mechanical expansion and contraction of an artery to pump working fluid, may be applied in other contexts which may or may not include a tumid implant device. Also, this disclosure appreciates that other pump designs, including battery-powered pumps or pumps with other power sources such as motion of the host organism, may be applied in combination with tumid implant devices described herein. Therefore, artery pump designs including bladder-type pumps, piston-type pumps, or other artery pumps may be used in connection with some embodiments of this disclosure. Other pump designs such as battery-powered pumps, positive displacement pumps, gravity pumps, and pumps that may be adapted from insulin or other medical pumps may be used in connection with some embodiments of this disclosure.

In some embodiments, tumid implants may comprise a tough, thin, flexible, generally round sack membrane which may be surgically inserted between the cartilage and meniscus of the knee. The sack membrane may contain fluid that may be pressurized by an artery pump, powered by the large popliteal artery which runs behind the knee joint. The increasing and decreasing pressure in the artery may allow the artery pump to produce a pressure in the sack membrane of around two psi, which pressure may exert a force of about five (5) to twenty (20) pounds, depending on the specific implementation, tending to separate the knee joint. When the host organism is not exerting a compressive force on the knee (e.g., in mid-step), fluid may flow into the sack membrane. When compressive force is exerted (e.g., when the foot lands when running), fluid may be expelled into the reservoir, absorbing energy and preventing excessively high pressure in the sack membrane. When the joint rotates, the sack membrane may decrease direct contact between bones of the joint because the sack membrane separates the joint, leading to decreased pain.

Because fluid may fill volumes of any shape, sack membranes may automatically bridge over meniscus tears and other irregularities in the joint.

Figure 6:
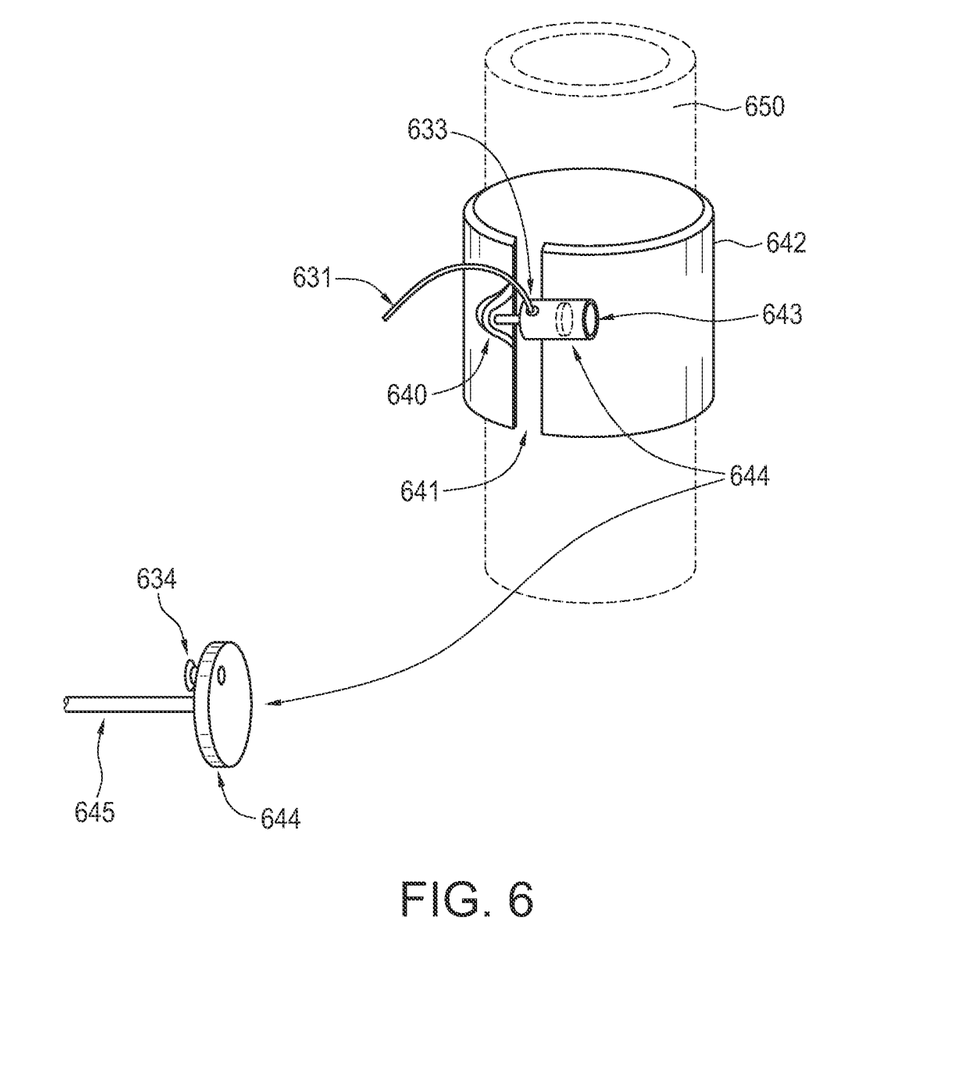
FIG. 6 is a diagram illustrating an example piston-type artery pump.

FIG. 6 is a diagram illustrating an example piston-type artery pump, arranged in accordance with at least some embodiments of the present disclosure. FIG. 6 includes a flexible cylindrical collar 642 adapted to substantially surround an artery segment 650. Collar 642 comprises a variable gap 641 oriented substantially parallel to a direction of blood flow through artery 650. Collar 642 may be adapted to flex in unison with expansion and contraction of artery 650, thereby expanding and contracting a width of variable gap 641 as artery 650 expands and contracts.

A piston pump 640 may be affixed on an outer surface of collar 642. Piston pump 640 extends across variable gap 641 and may be oriented substantially perpendicular to variable gap 641. Piston pump 640 comprises a piston pump housing 643 and a piston 644. Piston pump housing 643 may be affixed to collar 642 on a first side of variable gap 641, e.g., on the right side of variable gap 641 as illustrated in FIG. 6.

Piston 644 may be affixed to a piston rod 645. Piston rod 645 may be affixed at its other end to collar 642 on a second side of variable gap 641, e.g., on the left side of variable gap 641, opposite piston pump housing 643. Piston rod 645 extends into piston pump housing 643, for example through a pressure packing (not visible in FIG. 6), and piston rod 645 may be affixed to piston 644 within piston pump housing 643. Piston 644 is thereby adapted to slide back and forth within piston pump housing 643 in a direction substantially perpendicular to flow of blood through the artery, as the width of variable gap 641 expands and contracts.

As with the bladder-type artery pump described above with reference to FIG. 5, a first valve 504 may be adapted to allow flow of working fluid 206 out of piston pump 601, and a second valve 506 may be adapted to allow flow of working fluid 206 into piston pump 601. In the case of piston pump 601, a first valve 633 may be adapted to allow flow of working fluid out of piston pump housing 643 and to inhibit flow of working fluid into piston pump housing 643, and a second valve 634 may be adapted to allow flow of working fluid into piston pump housing 643 and to inhibit flow of working fluid out of the piston pump housing 643. First valve 633 may be coupled with pressure capillary 631, which may lead to reservoir as illustrated in FIG. 5. Second valve 634 may be coupled with an intake capillary, which may lead to a sack membrane and/or a lymph filter, as described in FIG. 5 and FIG. 7.

In some embodiments, such as that of FIG. 6, piston pump 640 may comprise a single action pump, e.g., a pump that expels fluid through pressure capillary 631 when piston 644 travels in a first direction within piston pump housing 643, and draws fluid through an intake capillary when piston 644 travels in a second direction within piston pump housing 643. In some embodiments, piston pump 640 may comprise a double action pump, e.g., a pump that simultaneously expels fluid through pressure capillary 631 and draws fluid through an intake capillary when piston 644 travels in any direction within piston pump housing 643.

Arrangements of sack membranes, reservoirs, pressure and intake capillaries, and first and second valves 633 and 634 in combination with piston pump 640 may generally incorporate any of the aspects and considerations described herein in connection with bladder-type artery pump designs. Piston pump 640 may be configured with a diameter of piston pump housing 643 and piston 644 that is suited to provide desired pressure and fluid flow rate outputs. In general, piston pump 640 may produce a wide range of pressures, and may be able to produce higher pressures than may be achievable with bladder-type artery pumps. In some embodiments, multiple piston pumps may be arranged on collar 642 and pressure capillaries extending from the multiple piston pumps may for example lead to a same reservoir or to multiple different reservoirs.

In some embodiments, piston pump 640 may comprise an injection molded apparatus which may be made for example from any of a variety of resins that are low in friction, such as nylon, tetrafluoroethylene, and/or polyacetal. Piston pump 640 may molded as one piece of low-friction resin, or piston 644 and piston pump housing 643 may be molded separately from collar 642 and then attached to piston pump housing 643, in which case the collar 642 may be of higher-friction material such a stainless steel or a different resin. Separate manufacture of piston 644 and piston pump housing 643 may allow the use of lower friction materials therein. Also, piston 644 and piston pump housing 643 may include piston rings and cylinder liners of different materials (not illustrated). Collar 642 may comprise materials that are both strong enough to resist circumferential stretching, and flexible enough to be snapped into place around artery 650. Piston rod 645 may be made in one piece with collar 642 or, may be made as a separate piece and snapped into place with a snap-fitting ball and socket connection. Any mechanical arrangement in which piston pump housing 643 moves with one end of the collar 642, while the piston 644 moves with the other end, will be effective for pumping.

Figure 7:
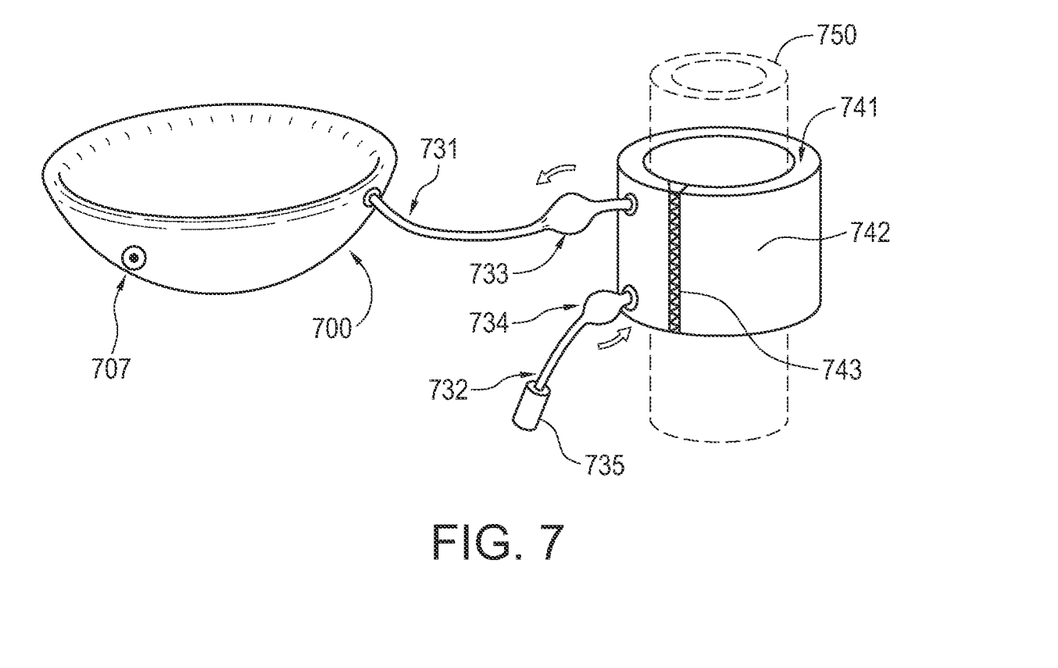
FIG. 7 is a diagram illustrating an example tumid implant device coupled with a pump, all arranged in accordance with at least some embodiments of the present disclosure.

FIG. 7 is a diagram illustrating an example tumid implant device coupled with a pump, arranged in accordance with at least some embodiments of the present disclosure. FIG. 7 includes a sack membrane 700 comprising a fluid release valve 707. Sack membrane 700 is coupled directly with a pressure capillary 731. Pressure capillary 731 includes a first valve 733 disposed inside pressure capillary 731. Pressure capillary 731 is coupled with a bladder-type artery pump comprising bladder 741, cuff 742, and a cuff joint 743. The bladder-type artery pump in FIG. 7 is coupled with an intake capillary 732. Intake capillary 732 includes second valve 734 disposed inside intake capillary 732. Intake capillary 732 is coupled with a lymph filter 735.

FIG. 7 illustrates multiple optional design variations which may be deployed, individually or in combination, in tumid implant and/or pump designs described herein. It will be appreciated with the benefit of this disclosure that the bladder-type artery pump illustrated in FIG. 7 may be replaced by a piston-type artery pump in some embodiments, or otherwise with any pump adapted to translate mechanical expansion and contraction of an artery to pump working fluid into sack membrane 700 and/or a reservoir coupled with sack membrane 700. Likewise, non-artery pumps such as battery powered pumps, or pumps according to any other implantable pump design may optionally be incorporated into embodiments according to FIG. 7.

In FIG. 7, sack membrane 700 comprises fluid release valve 707. Fluid release valve 707 may be configured to release fluid from sack membrane 700 into a host organism in which sack membrane 700 is implanted. In some embodiments, fluid release valve 707 may be configured to release fluid in response to increased pressure, e.g., pressure exceeding a design pressure for fluid release valve 707, in sack membrane 700. Fluid release valve 707 may thereby expel fluid from sack membrane 700 in response to, e.g., a host organism landing from a jump, stepping off a curb, or otherwise loading a joint in which sack membrane 700 is implanted. In some embodiments, fluid release valve 707 may be configured to release fluid at a low flow rate relative to the volume of sack membrane 700 under normal pressures within sack membrane 700. For example, fluid release valve 707 may be configured to release fluid at a rate that is replaceable by additional fluid from a pump. By releasing fluid under normal pressures within sack membrane 700, fluid release valve 707 may support circulation of fluid through sack membrane 700 as well as other components of a tumid implant device, such as a reservoir, when included.

In FIG. 7, intake capillary 732 is fitted with lymph filter 735. Embodiments according to FIG. 7 may use lymph as working fluid. Lymph filter 735 may comprise a filter with perforations or channels configured to absorb or otherwise conduct lymph, and while blocking or otherwise preventing other fluids and/or solid particles from entering the pump. The artery pump implant device in FIG. 7 may be adapted to draw lymph into the artery pump from a body in which the artery pump implant device is implanted, through lymph filter 735, intake capillary 732, and second valve 734. Materials appropriate for use in lymph filter 735 may include, but are not limited to, any sieve materials adapted for use in medical implant applications.

In FIG. 7, sack membrane 700 is coupled directly with pressure capillary 731. Some embodiments may provide direct coupling between sack membrane 700 and a pump, without a reservoir between sack membrane 700 and a pump. Additionally, in embodiments according to FIG. 7, a reservoir may be coupled to sack membrane 700 separately from pressure capillary 731, so that the reservoir is not between the pump and the sack membrane 700.

In FIG. 7, first and second valves 733 and 734 are illustrated inside capillaries 731 and 732, respectively. Embodiments may place first and second valves 733 and 734 at any appropriate locations within disclosed apparatus as will be appreciated. Also, cuff joint 743 is illustrated. Artery pump designs may comprise one or more cuff joints to allow installation. Cuff joint 743 may comprise means for bending, separating and/or re-attaching portions of cuff 742, such as hinges, latching structures, bonding materials, gluing surfaces, or stitching surfaces.

Materials appropriate for use in the various fittings disclosed herein, such as gate 421, first and second valves 533 and 534, and fluid release valve 707 may include, but are not limited to, plastics such as nylon, tetrafluoroethylene, rigid silicone, and/or polyacetal. Fittings may include gaskets made of elastomers such as silicones. Fittings may also be designed to snap into position on the structures on which they are deployed.

The foregoing detailed description has set forth various embodiments of the devices and/or processes via the use of diagrams and examples. Insofar as such diagrams and examples contain one or more functions and/or operations, it will be understood by those within the art that each function and/or operation within such diagrams and examples may be implemented, individually and/or collectively, by a wide range of operational methods by appropriately trained professionals using a wide range of equipment.

Those skilled in the art will recognize that it is common within the art to describe devices and/or processes in the fashion set forth herein, and thereafter use engineering practices to integrate such described devices and/or processes into surgical and other medical therapies. That is, at least a portion of the devices and/or processes described herein may be integrated into a surgical therapy via a reasonable amount of experimentation. Those having skill in the art will recognize that surgical therapy generally includes one or more surgical steps and operational methods which are commonly known and understood to take place under the best medical and surgical practices. It is to be understood that the devices and operations disclosed herein are merely examples and that in fact many other devices and operations may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain example techniques have been described and shown herein using various methods, devices and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

The invention claimed is:

1. A tumid implant device, comprising:
    an enclosed sack membrane adapted to fit between bones in a joint, the enclosed sack membrane comprising:
        a first concave layer adapted to fit adjacent a first bone in the joint; and
        a second concave layer adapted to fit adjacent a second bone in the joint;
        the first and second concave layers having a separation distance from one another and thereby applying a separation between the first and second bones in the joint;
        wherein the enclosed sack membrane is adapted to enclose a working fluid therein, wherein the working fluid comprises lymph, and wherein the enclosed sack membrane comprises a fluid release valve adapted to allow the working fluid to circulate out of the enclosed sack membrane;
    a pressure capillary adapted to conduct the working fluid from a pump into the enclosed sack membrane; and
    an intake capillary fitted with a lymph filter to draw lymph into the pump.

2. The tumid implant device of claim 1, wherein the enclosed sack membrane comprises an elastic material adapted to stretch in response to an increase in pressure applied between the bones in the joint, and adapted to contract in response to a release in pressure applied between the bones in the joint.

3. The tumid implant device of claim 1, wherein the pump is adapted to translate mechanical expansion and contraction of an artery to pump the working fluid into the enclosed sack membrane.

4. The tumid implant device of claim 3, wherein the pump comprises a flexible cylindrical bladder surrounding the artery, an inextensible cylindrical cuff surrounding the flexible cylindrical bladder, and a valve adapted to allow flow of the working fluid from the bladder into the enclosed sack membrane and adapted to inhibit flow of the working fluid from the enclosed sack membrane into the bladder.

5. The tumid implant device of claim 3, wherein the pump comprises:
    a flexible cylindrical collar substantially surrounding the artery, the flexible cylindrical collar having a variable width gap;
    a piston pump affixed across the variable width gap in the flexible cylindrical collar; and
    a valve adapted to allow flow of the working fluid from the piston pump into the enclosed sack membrane and adapted to inhibit flow of the working fluid from the enclosed sack membrane into the piston pump.

6. The tumid implant device of claim 1, wherein the joint is a human knee joint, the first bone is a femur, the second bone is a tibia, and wherein the first concave layer is adapted to fit adjacent an epiphysis section of the femur and the second concave layer is adapted to fit adjacent a meniscus and tibia in the knee.

7. The tumid implant device of claim 1, wherein the first and second concave layers are oriented with concavity facing a same direction.

8. The tumid implant device of claim 1, wherein the first and second concave layers have substantially elliptical boundaries.

9. The tumid implant device of claim 8, further comprising a reinforced curved boundary section adjoining the first and second concave layers around the elliptical boundaries thereof, wherein the reinforced curved boundary section comprises a reinforced curved section of the enclosed sack membrane between the first and the second concave layers such that articulation of the joint causes the first concave layer to move through a first portion of the reinforced curved boundary section into the second concave layer, and articulation of the joint causes the second concave layer to move through a second portion of the reinforced curved boundary section into the first concave layer.

10. A tumid implant device, comprising:
    an enclosed sack membrane adapted to fit between bones in a joint, the enclosed sack membrane comprising:
        a first concave layer adapted to fit adjacent a first bone in the joint;
        a second concave layer adapted to fit adjacent a second bone in the joint;
        the first and second concave layers having a separation distance from one another and thereby applying a separation between the first and second bones in the joint; and
        the first and second concave layers having substantially elliptical boundaries;
        wherein the enclosed sack membrane is adapted to enclose a working fluid therein;
    a gate in the enclosed sack membrane, wherein the gate is adapted to allow the working fluid in the enclosed sack membrane to escape in response to an increase in pressure applied between the bones in the joint, and wherein the gate is adapted to allow the working fluid to flow back through the gate and into the enclosed sack membrane in response to a release in pressure applied between the bones in the joint;
    a reservoir coupled with the gate and filled with the working fluid, so that the working fluid in the enclosed sack membrane escapes through the gate and into the reservoir in response to an increase in pressure applied between the bones in the joint; and
    a pressure capillary adapted to conduct the working fluid from a pump into the reservoir;
    wherein the pump is adapted to translate mechanical expansion and contraction of an artery to pump the working fluid into the reservoir.

11. The tumid implant device of claim 10, wherein the pump comprises a flexible cylindrical bladder surrounding the artery, an inextensible cylindrical cuff surrounding the flexible cylindrical bladder, and a valve adapted to allow flow of the working fluid from the bladder into the reservoir and adapted to inhibit flow of the working fluid from the reservoir into the bladder.

12. The tumid implant device of claim 10, wherein the pump comprises:
    a flexible cylindrical collar substantially surrounding the artery, the flexible cylindrical collar having a variable width gap;
    a piston pump affixed across the variable width gap in the flexible cylindrical collar; and
    a valve adapted to allow flow of the working fluid from the piston pump into the reservoir and adapted to inhibit flow of the working fluid from the reservoir into the piston pump.

13. A tumid implant device, comprising:
    an enclosed sack membrane adapted to fit between bones in a joint, the enclosed sack membrane comprising:
        a first concave layer adapted to fit adjacent a first bone in the joint;
        a second concave layer adapted to fit adjacent a second bone in the joint;
        the first and second concave layers having a separation distance from one another and thereby applying a separation between the first and second bones in the joint; and
        the first and second concave layers having substantially elliptical boundaries;
        wherein the enclosed sack membrane is adapted to enclose a working fluid therein;
    a gate in the enclosed sack membrane, wherein the gate is adapted to allow the working fluid in the enclosed sack membrane to escape in response to an increase in pressure applied between the bones in the joint to a pressure at or above a gate threshold pressure, and wherein the gate is adapted to allow the working fluid to flow back through the gate and into the enclosed sack membrane in response to a release in pressure applied between the bones in the joint; and
    a reservoir coupled with the gate and filled with the working fluid, so that the working fluid in the enclosed sack membrane escapes through the gate and into the reservoir in response to an increase in pressure applied between the bones in the joint;
    wherein the reservoir comprises an elastic material adapted to stretch to accommodate working fluid escaping the enclosed sack membrane in response to the increase in pressure applied between the bones in the joint, and wherein the stretched elastic material is adapted to apply a backpressure at the gate so that working fluid in the reservoir is forced through the gate and into the enclosed sack membrane under the backpressure in response to a release in pressure applied between the bones in the joint; and
    wherein the backpressure produces a pressure difference, between the reservoir and the enclosed sack membrane under normal pressure, and the gate is adapted to respond to the pressure difference to allow the working fluid in the enclosed sack membrane to flow back through the gate and into the enclosed sack membrane.

14. The tumid implant device of claim 13, further comprising a pressure capillary adapted to conduct the working fluid from a pump into the reservoir.

15. The tumid implant device of claim 14, further comprising the pump, wherein the pump is coupled with the pressure capillary and adapted to pump the working fluid into the reservoir.

16. The tumid implant device of claim 15, further comprising an intake capillary adapted to conduct the working fluid from the enclosed sack membrane into the pump.

17. The tumid implant device of claim 13, further comprising a reinforced curved boundary section adjoining the first and second concave layers around the elliptical boundaries thereof, wherein the reinforced curved boundary section comprises a reinforced curved section of the enclosed sack membrane between the first and the second concave layers such that articulation of the joint causes the first concave layer to move through a first portion of the reinforced curved boundary section into the second concave layer, and articulation of the joint causes the second concave layer to move through a second portion of the reinforced curved boundary section into the first concave layer.

18. The tumid implant device of claim 13, wherein the joint is a human knee joint, the first bone is a femur, the second bone is a tibia, and wherein the first concave layer is adapted to fit adjacent an epiphysis section of the femur and the second concave layer is adapted to fit adjacent a meniscus and tibia in the knee.

19. The tumid implant device of claim 13, wherein the first and second concave layers are oriented with concavity facing a same direction.

* * * * *